United States Patent
Jamart et al.

(10) Patent No.: US 10,035,122 B2
(45) Date of Patent: Jul. 31, 2018

(54) HEAT INSULATION MATERIAL BASED ON AEROGEL

(71) Applicants: UNIVERSITE DE LORRAINE, Nancy (FR); CENTRE NATIONAL DE LA RECHERCHE SCIENTIFIQUE, Paris (FR)

(72) Inventors: Brigitte Jamart, Vandoeuvre (FR); Alain Degiovanni, Nancy (FR); Sébastien Son, Marbache (FR); Yves Jannot, Troussey (FR); Guillaume Pickaert, Nancy (FR)

(73) Assignees: UNIVERSITE DE LORRAINE, Nancy (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 0 days.

(21) Appl. No.: 15/506,361

(22) PCT Filed: Aug. 28, 2015

(86) PCT No.: PCT/EP2015/069762
§ 371 (c)(1),
(2) Date: Feb. 24, 2017

(87) PCT Pub. No.: WO2016/030513
PCT Pub. Date: Mar. 3, 2016

(65) Prior Publication Data
US 2017/0252718 A1  Sep. 7, 2017

(30) Foreign Application Priority Data
Aug. 28, 2014 (FR) ..................... 14 58092

(51) Int. Cl.
| | |
|---|---|
| *B01J 13/00* | (2006.01) |
| *C07K 7/02* | (2006.01) |
| *C08G 69/00* | (2006.01) |
| *B27K 3/15* | (2006.01) |
| *B27K 3/02* | (2006.01) |
| *E04B 1/74* | (2006.01) |
| *C08L 97/02* | (2006.01) |
| *C07K 7/04* | (2006.01) |
| *D06M 13/342* | (2006.01) |
| *D06M 13/422* | (2006.01) |
| *D06M 13/35* | (2006.01) |
| *B27K 3/34* | (2006.01) |

(52) U.S. Cl.
CPC ......... *B01J 13/0091* (2013.01); *B27K 3/0278* (2013.01); *B27K 3/153* (2013.01); *B27K 3/343* (2013.01); *C07K 7/02* (2013.01); *C07K 7/04* (2013.01); *C08G 69/00* (2013.01); *C08L 97/02* (2013.01); *D06M 13/342* (2013.01); *D06M 13/35* (2013.01); *D06M 13/422* (2013.01); *E04B 1/74* (2013.01); *B27K 2200/10* (2013.01); *B27K 2240/70* (2013.01); *E04B 2001/742* (2013.01)

(58) Field of Classification Search
CPC .......... B01J 13/0091; C07K 7/04; C07K 7/02; D06M 13/342; D06M 13/422; D06M 13/35; B27K 3/343; B27K 3/153; B27K 3/0278; B27K 2240/70; B27K 2200/10; E04B 1/74; E04B 2001/742; C08G 69/00; C08L 97/02
See application file for complete search history.

(56) References Cited

U.S. PATENT DOCUMENTS

| | | | |
|---|---|---|---|
| 8,663,739 B2 | 3/2014 | Yeo et al. | |
| 2002/0094426 A1 | 7/2002 | Stepanian et al. | |
| 2012/0097884 A1* | 4/2012 | Jamart-Gregoire .. | C07D 221/06 252/62 |

FOREIGN PATENT DOCUMENTS

EP   2281961 A1   2/2011

OTHER PUBLICATIONS

Brosse et al. "A Family of Strong Low-Molecular-Weight Organogelators Based on Aminoacid Derivatives" Tetrahedron Letters (2004), 45(52), pp. 9521-9524.
Jannot et al., "Thermal Conductivity Measurement of Insulating Materials with a Three Layers Device" International Journal of Heat and Mass Transfer (2009), 52(5-6), pp. 1105-1111.
Jannot et al., "A Centered Hot Plate Method for Measurement of Thermal Properties of Thin Insulating Materials" Measurement Science and Technology (2010), 21(3), pp. 1-8.
French Search Report from French Patent Application No. 1458092, dated May 13, 2015.
International Search Report from International Patent Application No. PCT/EP2015/069762, dated Dec. 8, 2015.

* cited by examiner

*Primary Examiner* — John M Mauro
(74) *Attorney, Agent, or Firm* — Greer, Burns & Crain, Ltd.

(57) ABSTRACT

A heat insulation material is provided that is produced by drying a fibrous matrix impregnated with a solution of pseudo-peptides of formula (I), wherein: R is a side-chain of a natural or synthetic amino acid, R1 is either a linear or branched ($C_1$-$C_3$)alkyl group, or a linear or branched ($C_1$-$C_3$)alcoxy group, or an aryl group, or an aryl($C_1$-$C_3$)alkyl group, or an aryloxy group, or a saturated or unsaturated heterocycle, n=1 or 2, and A is an aromatic or heteroaromatic group with at least one cycle.

13 Claims, No Drawings

HEAT INSULATION MATERIAL BASED ON AEROGEL

BACKGROUND

The present invention relates to an aerogel-based thermal insulating material.

Aerogels are defined as dry gels generally having pores of nanometric volume. This type of material is obtained by the supercritical drying of organogels which makes it possible to eliminate the solvent while retaining the porous texture of the liquid gel.

In application WO2010/133798, the inventors previously described a series of organogelators derived from natural amino acids, allowing the formation of organic physical gels with a low molecular weight. The aerogels obtained from these organogelators by extraction of the solvent are mesoporous nanostructured materials which have remarkable properties, in particular in terms of specific surface area, very low solid contribution and thermal stability over time due to its very high hydrophobicity.

However, the aerogels described in application WO2010/133798 have neither the mechanical strength nor the density required in order to be used alone for certain applications, in particular such as insulating material in buildings.

As a result, there exists the need to develop thermal insulating materials having both the aerogel properties described in WO2010/133798, in particular hydrophobicity, and a better stiffness and physical strength.

Application US2002/0094426 describes a composite comprising an aerogel and a support matrix, for example a batting, obtained by implementing supercritical $CO_2$ extraction on said support matrix impregnated with a solution of a material capable of forming an inorganic gel, such as a silica gel or a polymeric gel.

Given that these gels are chemical gels held together by irreversible covalent bonds, the use thereof for impregnating a matrix presents certain drawbacks. In fact, once gelation is complete, it is no longer possible to correct a defect that has occurred during impregnation of the support matrix. Moreover, the composites described in this application require an additional chemical treatment in order to make the final products hydrophobic. In addition, polymerization of the polymeric gels also requires the addition of chemical complements.

Therefore, there is an industrial benefit in proposing thermal insulating materials which can be more easily manufactured.

SUMMARY

The objective of the invention is to overcome these technical shortcomings and to propose such a thermal insulating material.

In carrying out research on the aerogels described in WO2010/133798, the inventors discovered that, contrary to all expectations, a thermal insulating material meeting these requirements can be obtained by drying a fibrous matrix impregnated with the organogelators described in this application.

The material according to the invention obtained after drying is very hydrophobic and exempt from the additional treatments that are necessary for the composite described in US2002/0094426. It is even more surprising that the material according to the invention has a better physical strength and a higher density compared with the aforesaid non-impregnated fibrous matrix.

The invention relates to a thermal insulating material obtained by drying a fibrous matrix impregnated with a solution of pseudopeptides of formula (I),

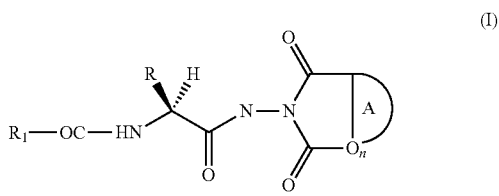

in which:
R represents a side chain of a natural or synthetic amino acid,
$R_1$ represents either a linear or branched $(C_1-C_8)$alkyl group, or a linear or branched $(C_1-C_8)$alkoxy group, or an aryl group, or an aryl$(C_1-C_4)$alkyl group, or an aryloxy group, or a saturated or unsaturated heterocycle, n=1 or 2 and
A represents an aromatic or heteroaromatic group with one or more rings,
said fibrous matrix having a low thermal conductivity of less than 0.05 W/m/K and a density of less than 50 kg/m$^3$.

The thermal conductivity of the final product is measured by methods well known to a person skilled in the art, using for example, the centred hot plate method (Y. Jannot, V. Felix, A. Degiovanni, Measurement Science and Technology 2010, 21, No. 035106) or the three layers method (Y. Jannot, G. Payet, A. Degiovanni, IJHMT 2009, 52, 1105-1111), finished by a centred hot plate measurement (Y. Jannot, V. Felix, A. Degiovanni, Measurement Science and Technology 2010, 21, No. 035106).

The preparation of the material of the invention is based on the complete penetration of the solution of pseudopeptides of formula (I) into the fibrous matrix and the prior formation of an intermediate "organogel/matrix" product, in which all of the cavities of the fibrous matrix are filled by the organogel formed by the pseudopeptides of formula (I).

Given that these organogels are thermoreversible physical gels, once the fibrous matrix is impregnated with the solution of pseudopeptides of formula (I), the intermediate "organogel/matrix" product can be simply obtained by cooling. Moreover, an impregnation defect which has appeared on the intermediate product can easily be corrected by heating.

Within the meaning of the present invention, by linear or branched $(C_1-C_8)$alkyl is meant a hydrocarbon-containing chain with 1 to 8 carbon atoms, in particular with 1 to 6 carbon atoms. Such as for example the groups: methyl, ethyl, propyl, isopropyl, butyl, isobutyl, sec-butyl, tert-butyl, pentyl, isopentyl, neopentyl, tert-pentyl, hexyl, isohexyl, 1,1-dimethylbutyl, 2,2-dimethylbutyl, 3,3- dimethylbutyl and 2-ethylbutyl.

Within the meaning of the present invention, by natural or synthetic amino acid is meant in particular the following amino acids: aspartic acid (Asp or D), asparagine (Asn or N), threonine (Thr or T), serine (Ser or S), glutamic acid (Glu or E), glutamine (Gln or Q), glycine (Gly or G), alanine (Ala or A), cysteine (Cys or C), valine (Val or V), methionine (Met or M), isoleucine (Ile or I), leucine (Leu or L), tyrosine (Tyr or Y), phenylalanine (Phe or F), histidine (His or H), lysine (Lys or K), tryptophan (Trp or W), praline (Pro or P) and arginine (Arg or R).

Within the meaning of the present invention, by aryl is meant a group selected from the group comprising phenyl, benzyl, tolyl, xylyl and naphthyl.

Within the meaning of the present invention, by saturated or unsaturated heterocycle or by heteroaromatic is meant a group selected from the group comprising oxiranyl, azetidinyl, oxetanyl, thietanyl, pyrrolidinyl, tetrahydrofuryl, thiolanyl, piperidyl, tetrahydropyranyl, morpholinyl, thiomorpholinyl and piperazinyl, pyridyl, pyrimidinyl, pyridazinyl, pyrrolyl, furanyl, thiophenyl, imidazolyl, pyrazolyl, isoxazolyl, isothiazolyl, thiazolyl, oxazolyl, 1,2,4-oxadiazolyl, 1,2,3-oxadiazolyl, 1,3,4-oxadiazoly 1,2,3-thiadiazolyl, 1,2,4-thiadiazolyl, 1,3,4-thiadiazolyl, 1,2,4-triazolyl, 1,3,4-triazolyl, 1,2,3-triazolyl and tetrazolyl; benzofuranyl, isobenzofuranyl, benzo[b]thienyl, indolyl, isoindolyl, 1H-indazolyl, benzimidazolyl, benzoxazolyl, benzisoxazolyl, benzothiazolyl, benzisothiazolyl, benzodioxolyl, 1H-benzotriazolyl, quinolyl, isoquinolyl, cinnolinyl, quinazolinyl, quinoxalinyl and phthalazinyl.

The pseudopeptides of formula (I) can be synthesized in three stages from natural or synthetic amino acids and inexpensive commercial reagents following standard techniques known to a person skilled in the art or described in the literature.

The organogels can also be obtained following standard techniques known to a person skilled in the art or described in the literature. By way of example, they can be prepared by heating a pseudopeptide of formula (I) to reflux in a solvent known to a person skilled in the art in proportions comprised between 0.01 and 5%, advantageously between 0.2 and 2% by weight of organogelators with respect to the solvents, followed by cooling.

Depending on the structure and the density of the fibrous matrix and the properties sought for the final product, the concentration of pseudopeptides of formula (I) in the solution can vary from 1% to 70% by weight.

In an advantageous embodiment of the thermal insulating material according to the invention, the aforesaid fibrous matrix is a matrix of plant, animal, mineral origin, of natural or synthetic polymers, or a matrix obtained by mixtures thereof.

In a more advantageous embodiment, said matrix is in particular selected from the group comprising a fibreboard, a blanket of wood fibres, a cotton, wool, mineral wool, polystyrene, polyurethane, polyisocyanate or polyisocyanurate matrix.

In another advantageous embodiment of the thermal insulating material according to the invention, the pseudopeptide of formula (I) is selected from those in which the group

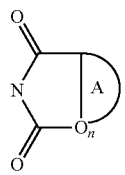

represents either a group

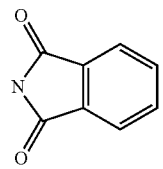 [SMILES: O=C1NC(=O)c2ccccc21]

or a group

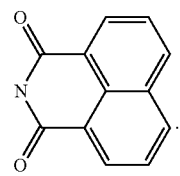

In a more advantageous embodiment of the thermal insulating material according to the invention, the pseudopeptide of formula (I) is selected from those in which R represents either —CH$_2$Ph, or —C(CH$_3$)$_3$, or —CH(CH$_3$)$_2$ and R$_1$ represents either PhCH$_2$O, or CH$_2$=CH—CH$_2$O.

In a particularly advantageous embodiment, the thermal insulating material according to the invention is obtained by drying a fibreboard impregnated with a solution of pseudopeptides of formula (Ia)

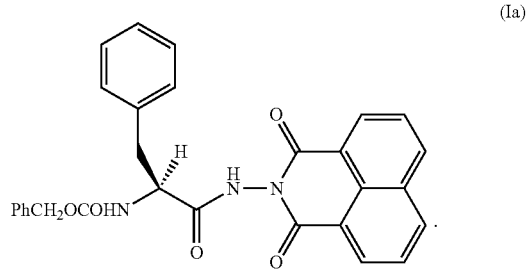

(Ia)

In a particularly advantageous embodiment, the thermal insulating material according to the invention is obtained by drying a blanket of wood fibres impregnated with a solution of pseudopeptides of formula (Ia)

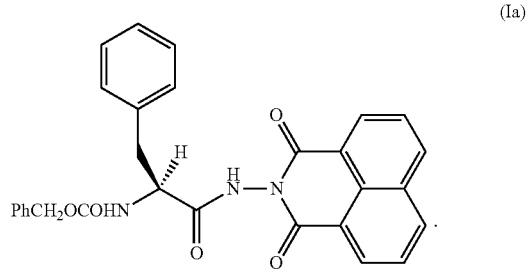

(Ia)

A purpose of the invention is also to make available a method for preparing an aforesaid thermal insulating material.

Said method comprises the following stages:
(i) preparing a liquid solution of pseudopeptides of formula (I), in particular of formula (Ia), in a solvent;

(ii) bringing an above-mentioned fibrous matrix into contact with a solution obtained in stage (i) until said matrix is completely impregnated with said solution and reaches its maximum capacity for absorbing said solution;

(iii) forming an organogel/matrix complex by cooling;

(iv) extracting the solvent contained in said organogel/matrix complex in order to obtain the aforesaid thermal insulating material.

The extraction of the solvent in the "organogel/matrix" complex can be carried out by any methods known in the art, in particular by drying in a supercritical $CO_2$ medium by standard techniques known to a person skilled in the art or described in the literature, such as for example that described in WO2010/133798.

The invention also relates to a thermal insulating material capable of being obtained by an aforesaid method.

Another aspect of the invention relates to the use of a solution of pseudopeptides of formula (I), in particular of formula (Ia), in order to improve the hydrophobicity of a fibrous matrix, in particular the hydrophobicity of a fibrous matrix having a low thermal conductivity and a density of less than 50 kg/m³.

The invention is illustrated in more detail by the example below.

EXAMPLE 1

Preparation of a Material According to the Invention

DETAILED DESCRIPTION

This example illustrates the preparation of a material of the invention obtained by drying a fibreboard impregnated with a solution of pseudopeptides of formula (Ia).

1. Materials and Methods
1.1. Characteristic of the Fibreboard

The fibreboard used in the example has a density of 43 kg/m³ and is in the form of square samples of 5×5 cm on each side.

1.2. Preparation of the Solution of Pseudopeptides of Formula (Ia)

A solution of pseudopeptides of formula (Ia) at 14.9% in 3-pentanol is prepared as follows:

2.14 g of the compound of formula (Ia) were dissolved hot in 15 mL of 3-pentanol in order to obtain a solution of the compound of formula (Ia) at 14.9% by weight. Solubilization is carried out for 2 minutes under stirring in a flask placed in a microwave oven offering the possibility of open reactor working. The working temperature of the microwave oven is set to 100° C. under a maximum power of 150 Watts. The flask is equipped with a water condensing system in order to condense the solvent vapours and to maintain the concentration of the solution.

The solution is maintained at a temperature greater than the sol-gel transition temperature, i.e. approximately 100° C. for a solution at 14.9%

1.3. Preparation of the "Fibreboard/Organogel" Composite

The fibreboard is placed in a stainless steel mould of the same dimension, which has been heated beforehand in order to avoid any thermal shock. The solution of the compound of formula (Ia) in 3-pentanol maintained at 100° C. is then poured onto the fibreboard. The mixture is cooled to ambient temperature until gelation of the gel. The "fibreboard/organogel" composite obtained is then extracted from the mould.

1.4. Drying the "Fibreboard/Organogel" Composite System

The composite obtained is dried according to the supercritical $CO_2$ drying process described in application WO2010/133798.

Said process is implemented in an autoclave (8 cm high, 100 ml volume) composed of a hollow, double-walled cylinder and two detachable ends composed of sintered metal allowing the passage of fluids.

The "fibreboard/organogel" composite is placed in an autoclave having a bed of beads covered with 0.5 g of 3-pentanol and maintained at 15° C. After closing the autoclave, the $CO_2$ previously cooled to 4° C. is introduced into the reactor under a pressure of 50 bar ($5 \times 10^6$ Pa). The pressure is then raised to 90 bar ($9 \times 10^6$ Pa) by injecting $CO_2$ using a diaphragm pump. The pressure of the first separator is set to 50 bar ($5 \times 10^6$ Pa) and that of the second separator to 20 bar ($2 \times 10^6$ Pa). The $CO_2$ flow rate is set to 400 g/h. The temperature of the separation elements is maintained at 20° C. during the entire drying process.

The temperature of the autoclave is then raised to 45° C. so as to cause the $CO_2$/3-pentanol system to pass to supercritical phase. After 20 minutes, the outlet valves of the autoclave and of the last separator are opened.

The continuous extraction of the 3-pentanol for 4 h with a $CO_2$ flow rate of 400 g/h makes it possible to obtain the expected "fibreboard/aerogel" composite.

2. Characteristics of the "Fibreboard/Aerogel" Product

The final "fibreboard/aerogel" product obtained has a density of 183 Kg/m³.

The thermal conductivity of the final product is measured by the three layers method (Y. Jannot, G. Payet, A. Degiovanni, IJHMT 2009, 52, 1105-1111), finished by a centered hot plate measurement (Y. Jannot, V. Felix, A. Degiovanni, Measurement Science and Technology 2010, 21, No. 35106).

The thermal conductivity of said final product measured at ambient temperature of approximately 25° C. is 0.026 W/m/K.

Said final product has a better mechanical strength compared to the organic aerogel alone described in application WO2010/133798 and to the fibreboard.

The density of the final product, which is approximately 183 kg/m³, is clearly greater than that of the organic aerogel alone described in application WO2010/133798 (2.83 kg/m³) and that of the fibreboard (43 kg/m³).

Moreover, said product has a better hydrophobicity than the fibreboard and close to that of the aerogel described in application WO2010/133798.

EXAMPLE 2

Preparation of a Material According to the Invention

This example illustrates the preparation of a material according to the invention obtained by drying a fibreboard impregnated with a solution of pseudopeptides of formula (Ia).

1. Materials and Methods
1.1. Characteristic of the Fibreboard

The fibreboard used in the example has a density of 43 kg/m³ and is in the form of square samples of 5×5 cm on each side.

1.2. Preparation of the Solution of Pseudopeptides of Formula (Ia)

A solution of pseudopeptides of formula (Ia) at 14.9% in 3-pentanol is prepared as follows:

2.14 g of the compound of formula (Ia) were dissolved hot in 15 mL of 3-pentanol in order to obtain a solution of the compound of formula (Ia) at 14.9% by weight. Solubilization is carried out for 2 minutes under stirring in a flask placed in a microwave oven offering the possibility of working in an open reactor. The working temperature of the microwave oven is set to 100° C. under a maximum power of 150 Watts. The flask is equipped with a water condensing system in order to condense the solvent vapours and to maintain the concentration of the solution.

The solution is maintained at a temperature greater than the sol-gel transition temperature, i.e. approximately 100° C. for a solution at 14.9%.

1.3. Preparation of the "Fibreboard/Organogel" Composite

The fibreboard is placed in a stainless steel mould of the same dimension, which has been heated beforehand in order to avoid any thermal shock. The solution of the compound of formula (Ia) in 3-pentanol maintained at 100° C. is then poured onto the fibreboard. The mixture is cooled to ambient temperature until gelation of the gel. The "fibreboard/organogel" composite obtained is then extracted from the mould.

1.4. Drying the "Fibreboard/Organogel" Composite System

The composite obtained is dried according to the supercritical $CO_2$ drying process described in application WO2010/133798.

Said process is implemented in an autoclave (8 cm high, 100 ml volume) composed of a hollow, double-walled cylinder and two detachable ends composed of sintered metal allowing the passage of fluids.

The "fibreboard/organogel" composite is placed in an autoclave having a bed of beads covered with 3.5 g of 3-pentanol and maintained at 15° C. After closing the autoclave, the $CO_2$ previously cooled to 4° C. is introduced into the reactor under a pressure of 50 bar ($5 \times 10^6$ Pa). The pressure is then raised to 90 bar ($9 \times 10^6$ Pa) by injecting $CO_2$ using a diaphragm pump. The pressure of the first separator is set to 50 bar ($5 \times 10^6$ Pa) and that of the second separator to 20 bar ($2 \times 10^6$ Pa). The $CO_2$ flow rate is set to 400 g/h. The temperature of the separation elements is maintained at 20° C. during the entire drying process.

The temperature of the autoclave is then raised to 45° C. so as to cause the $CO_2$/3-pentanol system to pass to supercritical phase. After 20 minutes, the outlet valves of the autoclave and of the last separator are opened.

The continuous extraction of the 3-pentanol for 4 h with a $CO_2$ flow rate of 400 g/h makes it possible to obtain the expected "fibreboard/aerogel" composite.

2. Characteristics of the "Fibreboard/Aerogel" Product

The final "fibreboard/aerogel" product obtained has a density of 183 Kg/m$^3$.

The thermal conductivity of the final product is measured by the three layers method (Y. Jannot, G. Payet, A. Degiovanni, IJHMT 2009, 52, 1105-1111), finished by a centred hot plate measurement (Y. Jannot, V. Felix, A. Degiovanni, Measurement Science and Technology 2010, 21, No. 35106).

The thermal conductivity of said final product measured at ambient temperature of approximately 25° C. is 0.026 W/m/K.

Said final product has a better mechanical strength compared to the organic aerogel alone described in application WO2010/133798 and to the fibreboard.

The density of the final product, which is approximately 183 kg/m$^3$, is clearly greater than that of the organic aerogel alone described in application WO2010/133798 (2.83 kg/m$^3$) and that of the fibreboard (43 kg/m$^3$). Moreover, said product has a better hydrophobicity than the fibreboard and close to that of the aerogel described in application WO2010/133798.

EXAMPLE 3

Preparation of a Material According to the Invention

This example illustrates the preparation of a material of the invention obtained by drying a blanket of untreated wood fibres impregnated with a solution of pseudopeptides of formula (Ia).

1. Materials and Methods 1.1. Characteristic of the Untreated Wood Fibres

The wood fibres used in the example are fine and untreated from the industrial defibration of wood.

1.2. Preparation of the Solution of Pseudopeptides of Formula (Ia)

A solution of pseudopeptides of formula (Ia) at 13% in 3-pentanol is prepared as follows:

1.23 g of the compound of formula (Ia) were dissolved hot in 10 mL of 3-pentanol in order to obtain a solution of the compound of formula (Ia) at 13% by weight. Solubilization is carried out for 2 minutes under stirring in a flask placed in a microwave oven offering the possibility of working in an open reactor. The working temperature of the microwave oven is set to 100° C. under a maximum power of 150 Watts. The flask is equipped with a water condensing system in order to condense the solvent vapours and to maintain the concentration of the solution.

The solution is maintained at a temperature greater than the sol-gel transition temperature, i.e. approximately 100° C. for a solution at 13%.

1.3. Preparation of the "Blanket of Wood Fibres/Organogel" Composite

The untreated wood fibres are placed and packed into an aluminium mould of dimensions 45 mm×45 mm×5 mm, which has been heated beforehand in order to avoid any thermal shock. The solution of the compound of formula (Ia) in 3-pentanol maintained at 100° C. is then injected into the mould, thus impregnating the blanket of wood fibres. The mixture is cooled to ambient temperature until gelation of the system. The "blanket of wood fibres/organogel" composite obtained is then extracted from the mould.

1.4. Drying the "Blanket of Wood Fibres/Organogel" Composite System

The composite obtained is dried according to the supercritical $CO_2$ drying process described in application WO2010/133798.

Said process is implemented in an autoclave (8 cm high, 100 ml volume) composed of a hollow, double-walled cylinder and two detachable ends composed of sintered metal allowing the passage of fluids.

The "blanket of wood fibres/organogel" composite is placed in an autoclave having a bed of beads covered with 3.5 g of 3-pentanol and maintained at 15° C. After closing the autoclave, the $CO_2$ previously cooled to 4° C. is introduced into the reactor under a pressure of 50 bar ($5 \times 10^6$ Pa). The pressure is then raised to 90 bar ($9 \times 10^6$ Pa) by injecting $CO_2$ using a diaphragm pump. The pressure of the first separator is set to 50 bar ($5 \times 10^6$ Pa) and that of the second separator to 20 bar ($2 \times 10^6$ Pa). The $CO_2$ flow rate is set to 400 g/h. The temperature of the separation elements is maintained at 20° C. during the entire drying process.

The temperature of the autoclave is then raised to 45° C. so as to cause the $CO_2$/3-pentanol system to pass to supercritical phase. After 20 minutes, the outlet valves of the autoclave and of the last separator are opened.

The continuous extraction of the 3-pentanol for 4 h with a $CO_2$ flow rate of 400 g/h makes it possible to obtain the expected "blanket of wood fibres/aerogel" composite.

2. Characteristics of the "Blanket of Wood Fibres/Aerogel" Product

The final "blanket of wood fibres/aerogel" product obtained has a density of 143 $Kg/m^3$.

The thermal conductivity of the final product is measured by the centred hot plate method (Y. Jannot, V. Felix, A. Degiovanni, Measurement Science and Technology 2010, 21, No. 35106).

The thermal conductivity of said final product measured at ambient temperature of approximately 25° C. is 0.025 W/m/K.

The invention claimed is:

1. A thermal insulating material obtained by drying a fibrous matrix impregnated with a solution of pseudopeptides of formula (I),

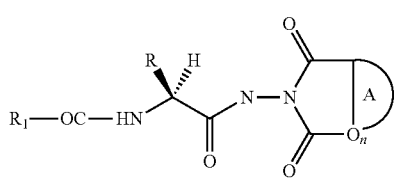
(I)

in which
R represents a side chain of a natural amino acid;
$R_1$ represents either a linear or branched $(C_1-C_8)$alkyl group, or a linear or branched $(C_1-C_8)$alkoxy group, or an aryl group, or an aryl$(C_1-C_4)$alkyl group, or an aryloxy group, or a saturated or unsaturated heterocycle, or $PhCH_2O$— or $CH_2$=CH—$CH_2O$—, n=1 or 2; and
A represents an aromatic or heteroaromatic group with one or more rings,
said fibrous matrix having a thermal conductivity of less than 0.05 W/m/K and a density of less than 50 $kg/m^3$.

2. The thermal insulating material according to claim 1, characterized in that the pseudopeptide of formula (I) is selected from those in which the group

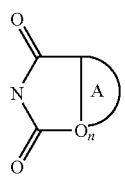

represents either a group

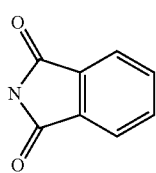 [SMILES: O=C1NC(=O)c2ccccc21]

or a group

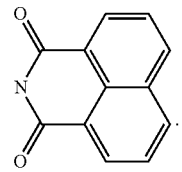

3. The thermal insulating material according to claim 1, characterized in that the pseudopeptide of formula (I) is selected from those in which R represents either —$CH_2Ph$, or —$C(CH_3)_3$ or —$CH(CH_3)_2$ and $R_1$ represents either $PhCH_2O$— or $CH_2$=CH—$CH_2O$—.

4. The thermal insulating material according to claim 1, characterized in that said fibrous matrix is a matrix of plant, animal, mineral origin, of natural or synthetic polymers, or any combination thereof.

5. The thermal insulating material according to claim 4, characterized in that said matrix is selected from the group consisting of a fibreboard, a blanket of wood fibres, a cotton, wool, mineral wool, polystyrene, polyurethane, polyisocyanate and polyisocyanurate matrix.

6. The thermal insulating material according to claim 1, characterized in that said material is obtained by drying a fibreboard impregnated with a solution of pseudopeptide of formula (Ia) or a blanket of wood fibres impregnated with a solution of pseudopeptide of formula (Ia)

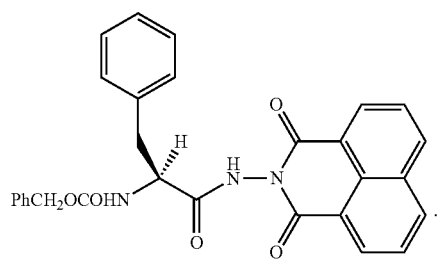
(Ia)

7. A method for preparing a thermal insulating material according to claim 1, wherein said method comprises the following stages:
(i) preparing a liquid solution of pseudopeptides of formula (I), in a solvent;
(ii) bringing a matrix as described according to claim 1 into contact with the solution obtained in stage (i) until said matrix is completely impregnated with said solution and reaches its maximum capacity for absorbing said solution;
(iii) forming an organogel/matrix complex by cooling; and
(iv) extracting the solvent contained in said organogel/matrix complex in order to obtain the aforesaid thermal insulating material.

8. A thermal insulating material obtained by the method according to claim 7.

9. The method according to claim 7, wherein step (i) is performed by preparing a liquid solution of pseudopeptide of formula (Ia)

(Ia)

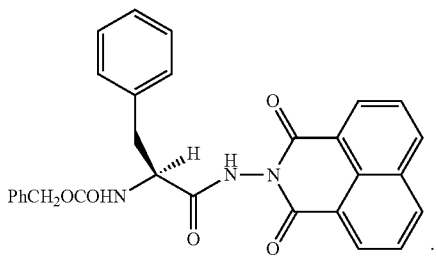

represents either a group

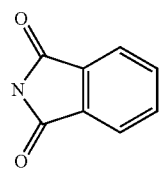

10. A method for improving the hydrophobicity of a fibrous matrix, said method comprising the following step: applying to said fibrous matrix a solution of pseudopeptides of formula (I):

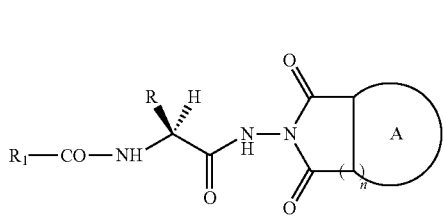 (I)

or a group

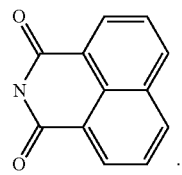

in which
R represents a side chain of a natural amino acid;
$R_1$ represents either a linear or branched $(C_1-C_8)$alkyl group, or a linear or branched $(C_1-C_8)$alkoxy group, or an aryl group, or an aryl$(C_1-C_4)$alkyl group, or an aryloxy group, or a saturated or unsaturated heterocycle, or PhCH$_2$O— or CH$_2$=CH—CH$_2$O—, n=1 or 2; and
A represents an aromatic or heteroaromatic group with one or more rings,
said fibrous matrix having a thermal conductivity of less than 0.05 W/m/K and a density of less than 50 kg/m³.

11. The method of claim 10, wherein the pseudopeptide of formula (I) is selected from those in which the group

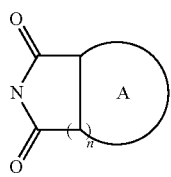

12. The method of claim 10, characterized in that the pseudopeptide of formula (I) is selected from those in which R represents either —CH$_2$Ph, or —C(CH$_3$)$_3$ or —CH(CH$_3$)$_2$ and $R_1$ represents either PhCH$_2$O— or CH$_2$=CH—CH$_2$O—.

13. The method of claim 10, where the solution of pseudopeptides of formula (I) is a solution of (Ia)

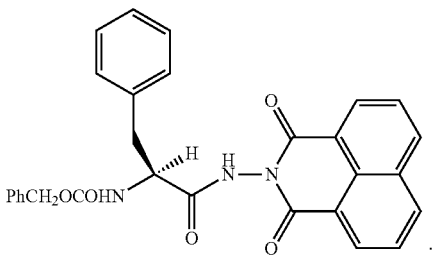 (Ia)

* * * * *